Figure 1:
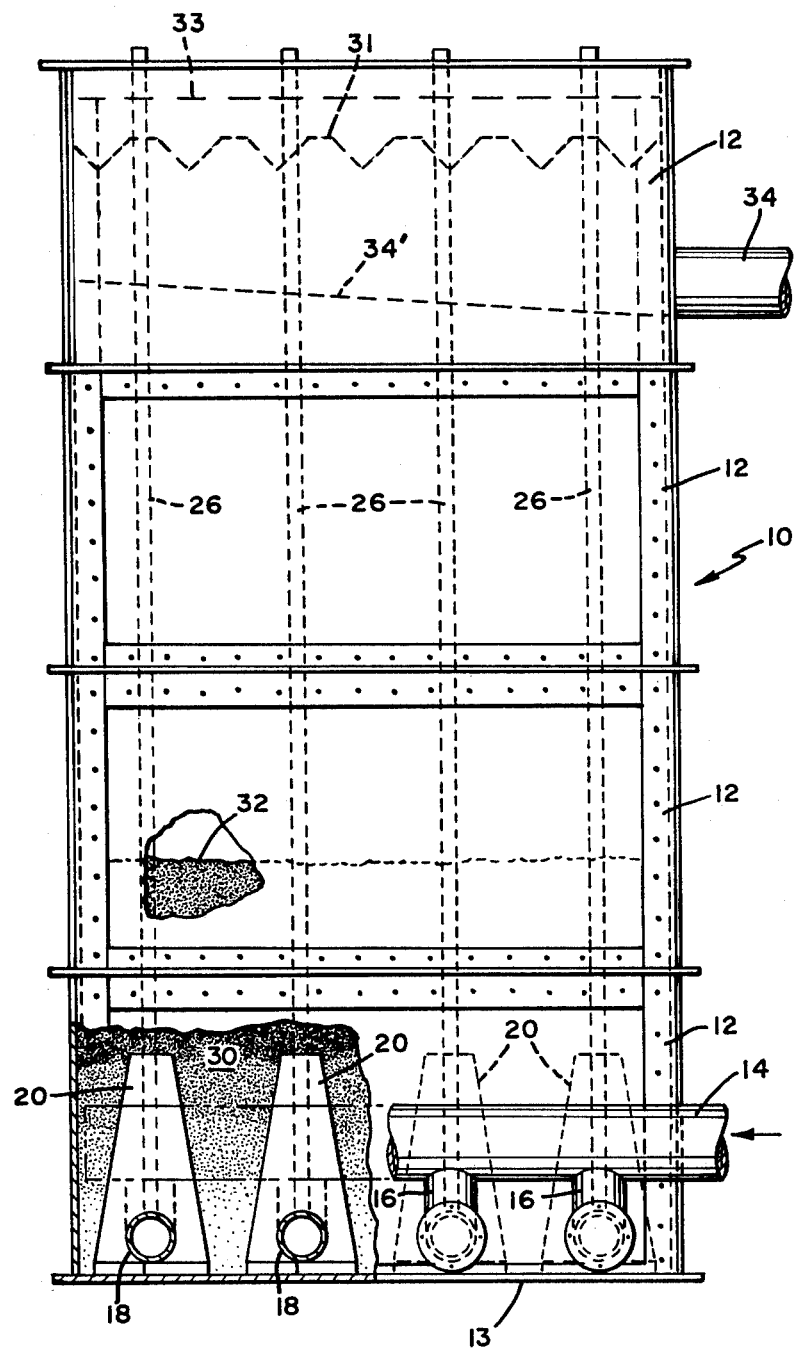

United States Patent [19]

Kos

[11] 4,202,774

[45] May 13, 1980

[54] FLOW DISTRIBUTOR FOR FLUID BED BIOLOGICAL REACTOR

[75] Inventor: Peter Kos, Ridgefield, Conn.

[73] Assignee: Dorr-Oliver Incorporated, Stamford, Conn.

[21] Appl. No.: 909,076

[22] Filed: May 24, 1978

[51] Int. Cl.² .................... B01D 23/18; B01D 41/02
[52] U.S. Cl. .................................. 210/274; 210/279; 210/293
[58] Field of Search ............... 210/274, 279, 291, 292, 210/293; 422/143, 311

[56] References Cited

U.S. PATENT DOCUMENTS

| | | | |
|---|---|---|---|
| 329,330 | 10/1885 | Matthiessen et al. | 210/291 X |
| 402,543 | 4/1889 | Roeske | 210/274 X |
| 1,429,477 | 9/1922 | Williamson | 210/292 |
| 1,544,617 | 7/1925 | Wagner | 210/293 |
| 2,678,874 | 5/1954 | Parker et al. | 422/143 X |
| 2,948,400 | 8/1960 | Hagen | 210/293 X |
| 3,298,793 | 1/1967 | Mallison et al. | 422/143 |
| 3,831,761 | 8/1974 | Chantereau | 210/279 X |
| 3,846,305 | 11/1974 | Schreiber et al. | 210/279 X |
| 4,090,852 | 5/1978 | Dowd | 422/143 |

FOREIGN PATENT DOCUMENTS

| | | | |
|---|---|---|---|
| 833628 | 3/1952 | Fed. Rep. of Germany | 210/292 |
| 830126 | 7/1938 | France | 210/291 |

*Primary Examiner*—Robert H. Spitzer
*Attorney, Agent, or Firm*—Burtsell J. Kearns; Harold M. Snyder

[57] ABSTRACT

A flow distributor for a fluid bed reactor includes means for decreasing velocity of incoming liquid streams in a uniform, non-turbulent fashion. Inlet ports communicate with fluid portals having divergent walls to slow incoming flow. The fluid portals feed liquid flow to a plurality of diffusing flow paths provided between diffusion baffles positioned at the bottom of the reactor. The diffusion baffles may be prismatic shapes which are trapezoidal in cross-section with the broadest horizontal dimension at the bottom thereof. The diffusion flow paths therefore have divergent walls and act to further slow the liquid flow passing therethrough.

17 Claims, 16 Drawing Figures

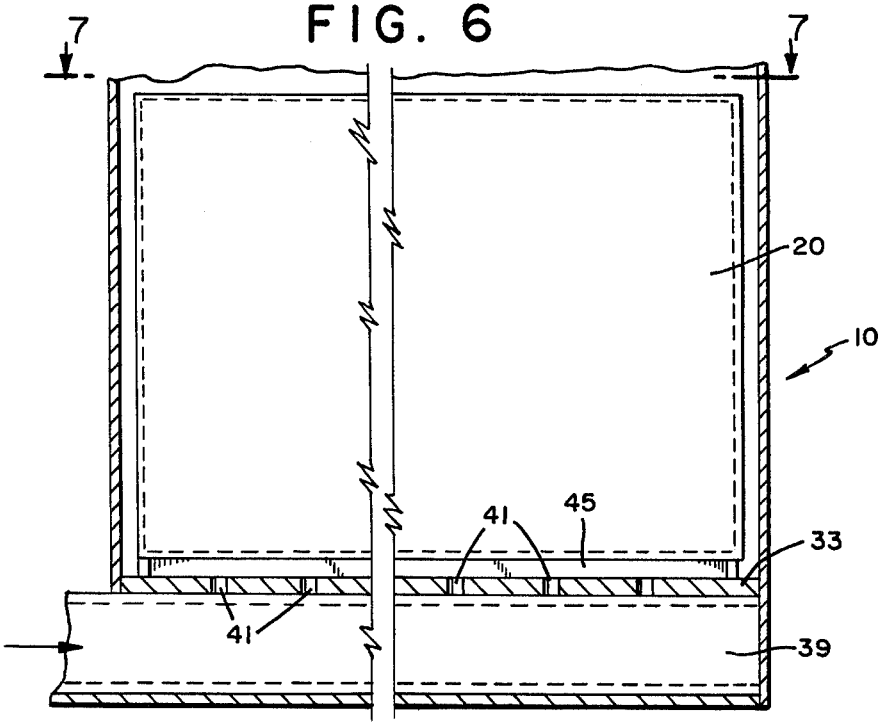
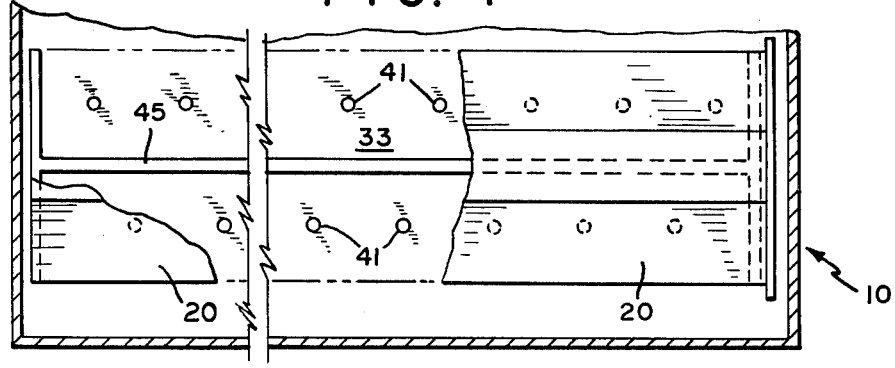
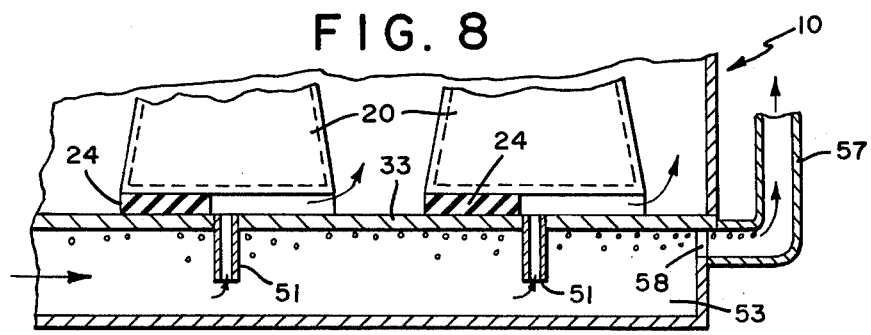

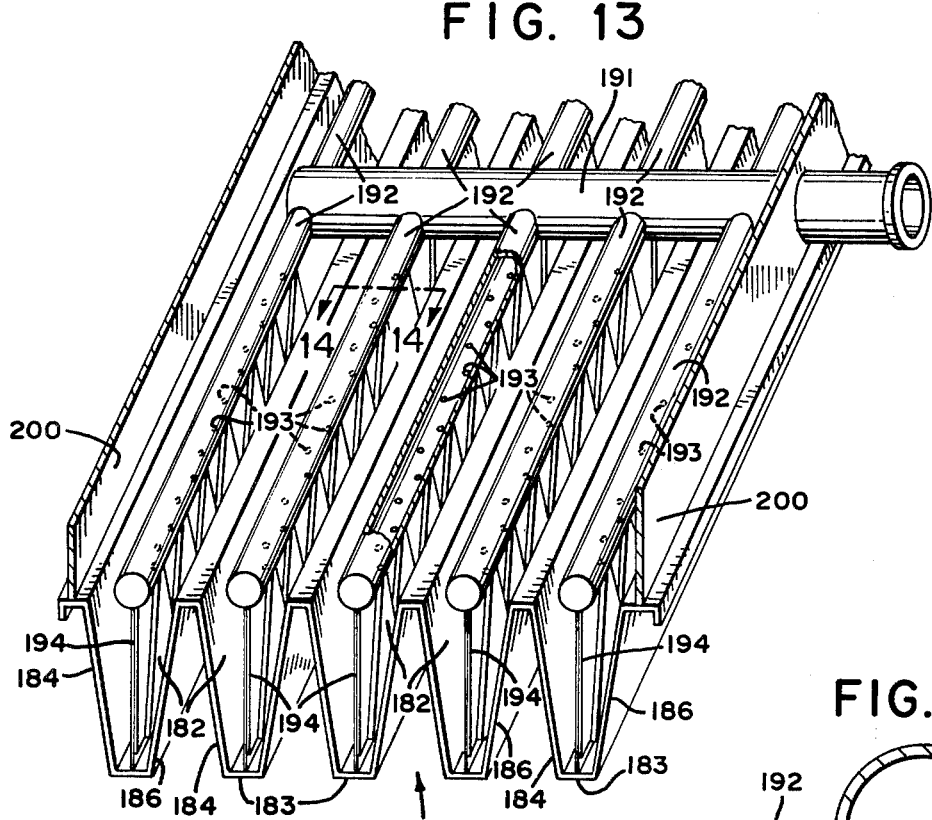
FIG. 13
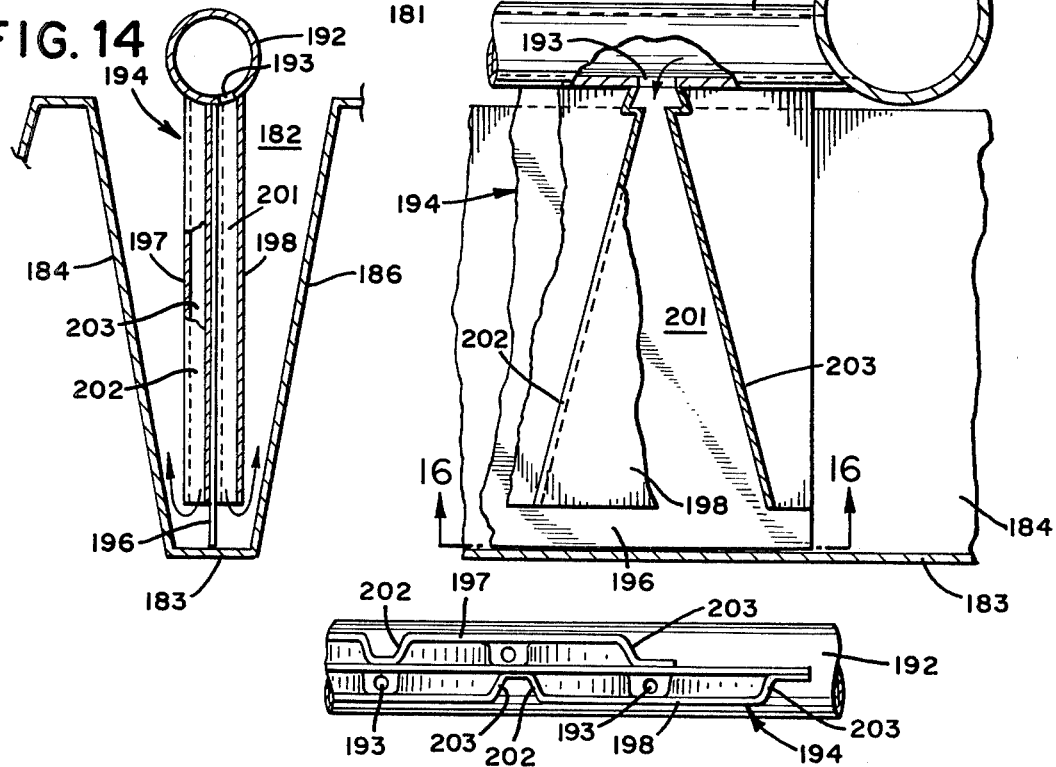
FIG. 14
FIG. 15
FIG. 16

FLOW DISTRIBUTOR FOR FLUID BED BIOLOGICAL REACTOR

This invention is directed to an apparatus for introducing liquid into a fluid bed reactor in a manner to enhance operation of the reactor.

Fluid bed biological reactors have recently been proposed to supplement or replace traditional biological reactors such as are used in the activated sludge or trickling filter processes for BOD removal, nitrification and denitrification. The basic principles of operation of the fluid bed biological reactors are advanced and covered in a series of patents including U.S. Pat. No. 3,846,289, issued Nov. 5, 1974, U.S. Pat. No. 3,956,129, issued May 11, 1976, U.S. Pat. No. 4,009,099, issued Feb. 22, 1977, U.S. Pat. No. 4,009,105, issued Feb. 22, 1977, and U.S. Pat. No. 4,009,098, issued Feb. 22, 1977.

The above patents point out that, in a fluidized bed environment, where solid particles, such as sand, form a bed which is suspended in an upwardly flowing liquid stream with the particles in continuous motion, an enormous surface area for biological growth is available. When appropriate conditions of temperature, pH, availability of food, absence or presence of oxygen, are maintained, biological growth is remarkably rapid so that the reactor volume required and the retention time necessary to achieve a given growth rate are drastically reduced. Accordingly, then, substitution of fluid bed biological reactors for the reactors in common use today, gives promise that the land area now devoted to sewage treatment plants, can, in the future, be significantly reduced.

While fluidization and suspension of the particulate solids is extremely important in fluid bed biological processes, since by this means the inert particles are exposed on all sides to the liquid waste so that biological growth occurs upon the whole surface area of the particles, it must be understood that excessive agitation will result in multiplying the contacts between particles with resultant abrasion and removal of the biological growth. This effect is particularly damaging when the tubulence occurs near the bottom of the tank where particulate solids with little or no biological growth tend to accumulate (since particles with substantial biological growth thereon are lighter and tend to rise in the bath). When these particulate solids, with little or no biological growth are exposed to an excessively turbulent environment, incipient biological growth will be quickly abraded away and the performance of the biological reactor will be adversely affected. Of course, sufficient liquid waste must be introduced into the reactor to completely fluidize the particulate solids therein.

A novel structure has now been provided in a fluid bed biological reactor which assures a smooth, low-turbulent flow of liquid into the reactor to fluidize particulate solids therein.

It is the object of this invention to provide in a fluid bed reactor improved flow distribution whereby excessive turbulence does not occur upon admission of liquid.

Figure 2:
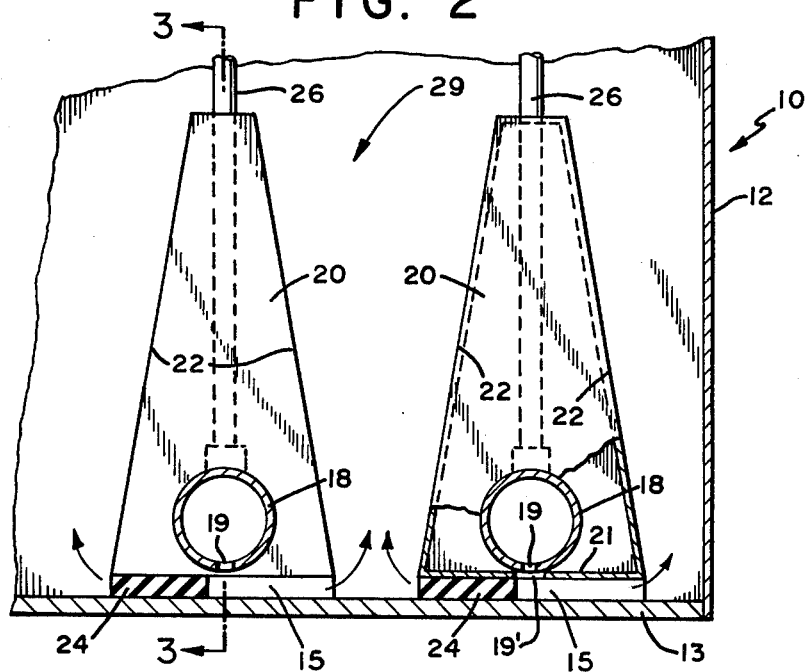
Figure 3:
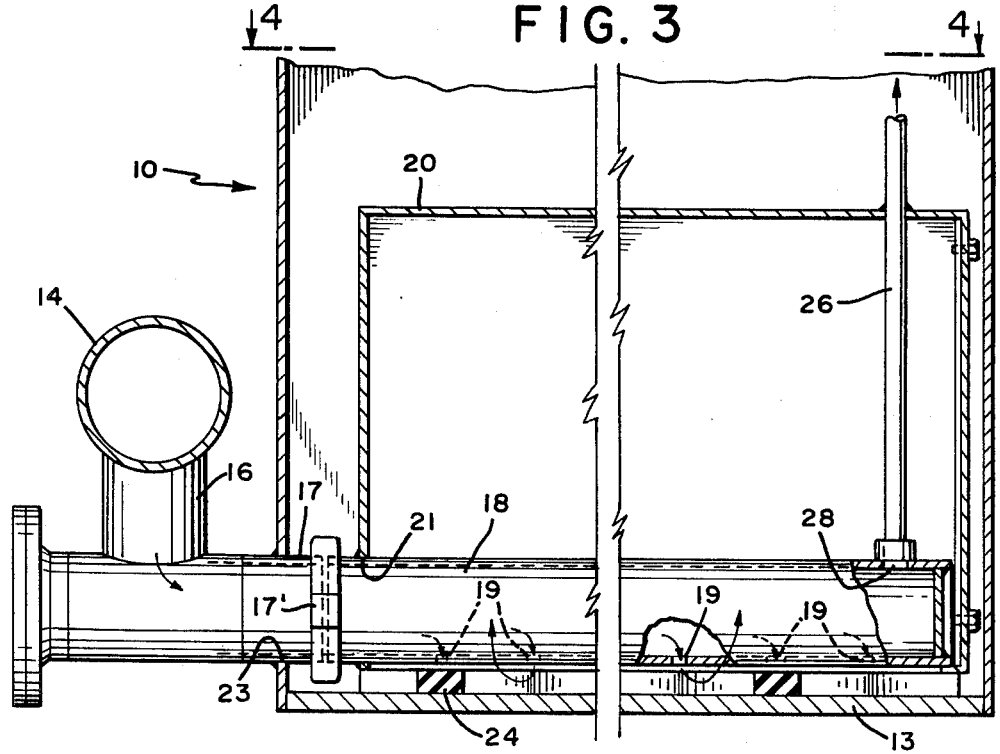
Figure 4:
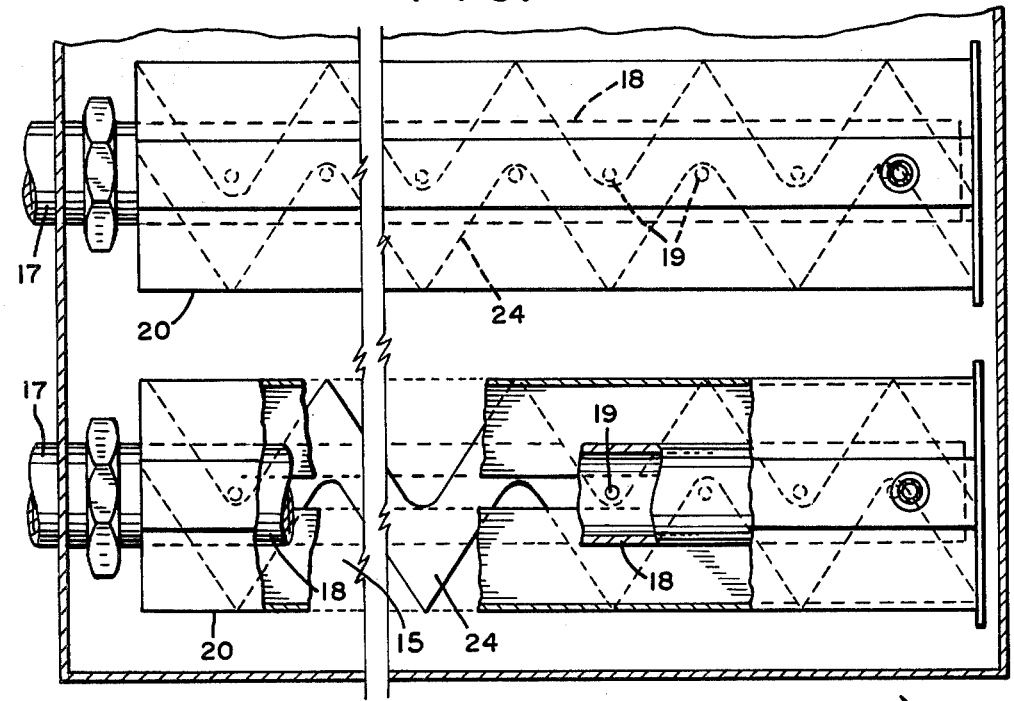
Figure 5:
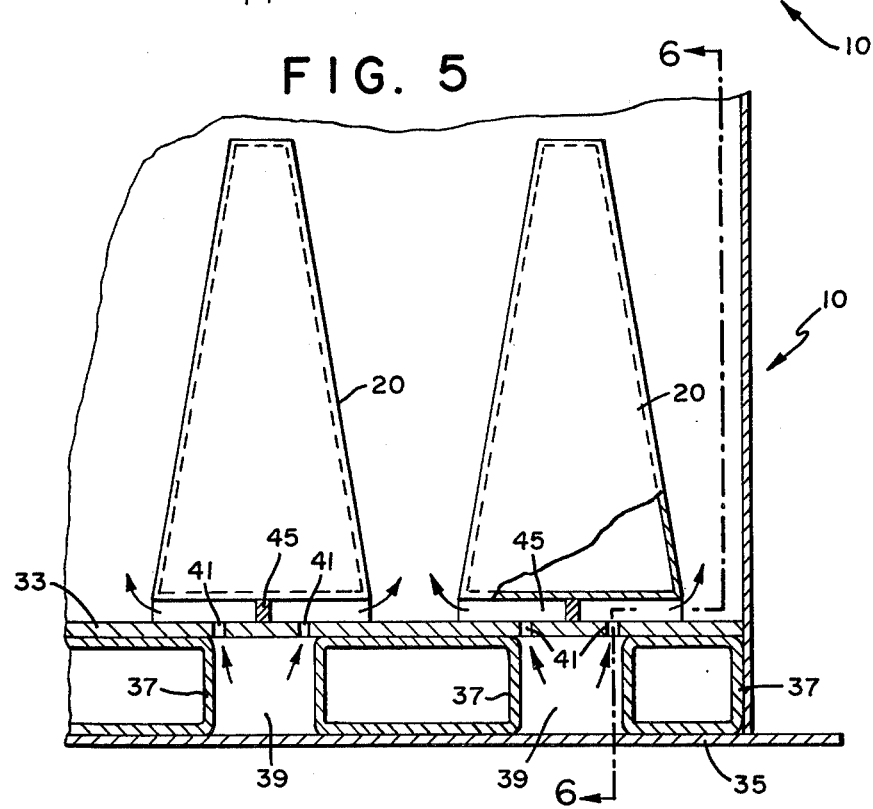
Figure 9:
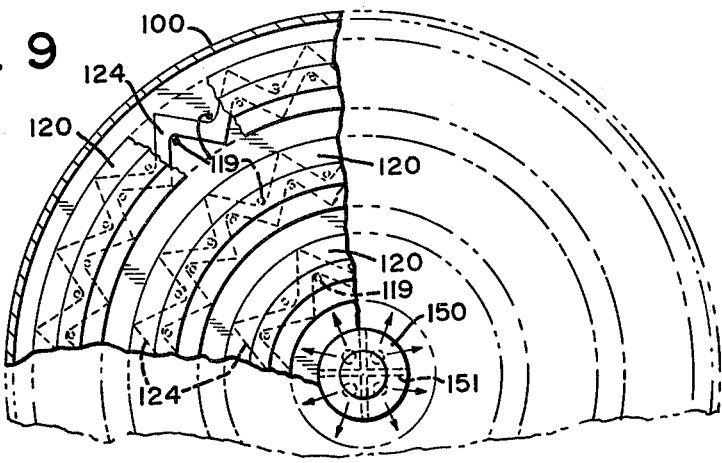
Figure 10:
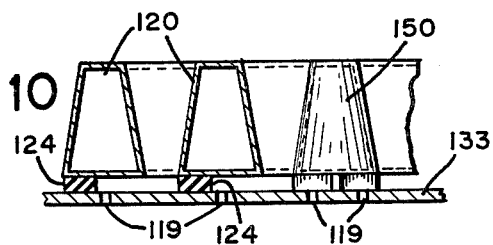
Figure 11:
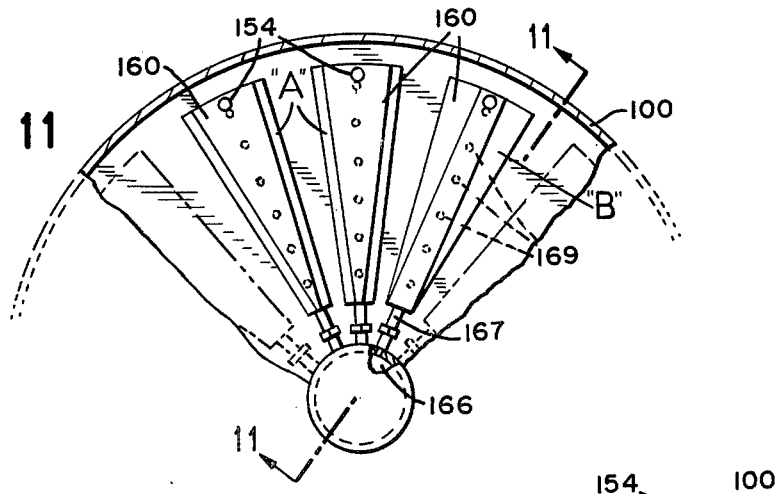
Figure 12:
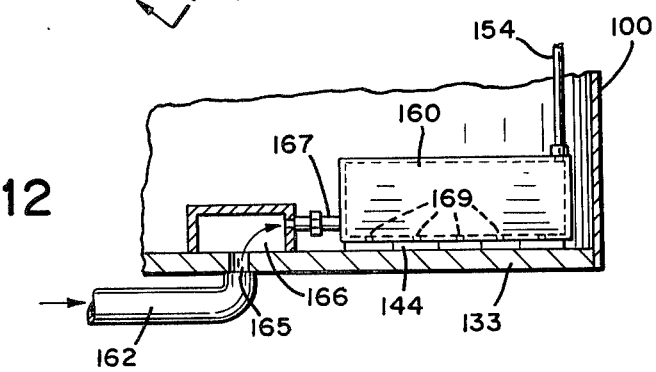

Other objects and advantages will become apparent from the following description taken in conjunction with the accompanying drawings in which:

FIG. 1 is a view in elevation of a fluid bed biological reactor incorporating the flow distributor of this invention with portions of the structure broken away to show the particulate solids bed within the reactor, FIG. 2 is a view in elevation of the diffusion baffles of the flow distributor with portions thereof shown in section, FIG. 3 is a view partially in section taken along line 3—3 of FIG. 2, FIG. 4 is a view taken along line 4—4 of FIG. 3 showing the diffusion baffles with portions thereof shown in section and broken away, FIG. 5 is a view similar to FIG. 2 of a modified embodiment of the diffusion baffles and associated structure, FIG. 6 is a view of the diffusion baffles and associated structure taken along line 6—6 of FIG. 5, FIG. 7 is a view of the diffusion baffle taken along line 7—7 of FIG. 6, with portions broken away, showing the configuration and location of the port structure, FIG. 8 is an elevational view partially in section of a modified form of the structure associated with the diffusion baffles, FIG. 9 is a plan view, partially broken away, of another embodiment of the flow distributor of the invention wherein the diffusion baffles are arranged in concentric circles in a circular tank, FIG. 10 is a fragmentary section in elevation of the flow distributor of FIG. 9, FIG. 11 is a further embodiment of the flow distributor of the invention wherein the diffusion baffles are arranged in a radial pattern in a circular tank, FIG. 12 is an elevational view partially in section of a radial diffusion baffle and associated structure.

FIG. 13 is a view in perspective of a further embodiment of the flow distributor of the invention, FIG. 14 is a view in section taken along 14—14 of FIG. 13, FIG. 15 is a fragmentary elevational view with portions shown in section of the fluid portal with associated structure, FIG. 16 is a view taken along line 16—16 of FIG. 15.

Generally speaking, the flow distributor of this invention is located in the lower portion of a fluid bed reaction tank and functions to accept liquid from an inlet and introduce that liquid into the reaction tank through a plurality of ports. Fluid portals are provided, each communicating with at least one of said ports and constituting a walled divergent flow path of increasing cross-sectional area with increasing distance from a communicating port. The fluid portals are oriented within the reaction tank so that the flow of liquid therein is directed at an angle in the range from the horizontal to vertically downward in the tank. Flow diffusers, having flow-confining walls, are provided each in fluid communication with a fluid portal and oriented to direct flow from the fluid portal in a generally vertically upward direction in said reaction tank, to fluidize the particulate solids without excessive turbulence. Preferably, the flow diffuser has upwardly divergent walls within which the velocity of the liquid smoothly and uniformly decreases as it progresses upwardly in the reaction tank.

In more specific terms, the flow distributor of the invention may include a plurality of diffusion baffles at the bottom of the reaction tank. These diffusion baffles are of a prismatic configuration having a trapezoidal cross-section. The axis of symmetry of the trapezoidal cross-section is vertically oriented in the reactor with the vertical dimension thereof exceeding about twice the broadest horizontal dimension of the cross-section. The broadest horizontal dimension of the trapezoidal cross-section is at the lower extremity of the diffusion baffles at or closely adjacent to the bottom of the reactor tank. The bottom of the tank thus presents the aspect of a number of prismatic shapes which are upwardly tapered and adjacent to one another. The space between adjacent diffusion baffles constitutes a flow path formed by the diverging sides of adjacent baffles. This flow path becomes greater in cross-section as distance from the bottom of the tank increases. The included angle between the divergent sides of adjacent diffusion baffles is from 5° to 30°.

While the discussion below is primarily directed to fluid bed reactors carrying out biological processes, the flow distributor of the invention is quite suitable for use in fluid bed reactors which are to be applied to enzymatic, ion exchange and adsorption processes. Thus, not only fluid bed biological processes, such as treatment of municipal and industrial waste, but also fluid bed processes for fermentation, water softening and adsorption with activated carbon may be improved by the apparatus of the invention.

Turning now to FIGS. 1 through 4, there is illustrated a biological fluid bed reactor tank 10 which, with appropriate modification, can be utilized to carry out separately or in combination the biological waste water treatment processes of BOD removal, nitrification and denitrification. The tank 10 is composed of a number of modular units 12. The modular units 12, as will be appreciated, can be assembled to produce tanks of required depth and volume. As illustrated in FIG. 1 the modules shown may be, for example, 4 feet wide, 2 feet high, and 1 foot in depth. Within tank 10 there is provided a body of particulate solids 30, such as, for example, sand, which is shown in FIG. 1 at the level occupied by the bed in the quiescent state as indicated by the top surface 32. The tank 10 has a bottom plate 13 which supports the bed of particulate solids 30 and the liquid waste undergoing treatment. A flow distributor is provided within or associated with the lowest of the modules 12 and comprises a waste fluid inlet 14 which is manifolded to a plurality of T-joints 16 which are in turn each connected to a nipple 17 secured in port 23 in the wall of tank 10. The nipple 17 is connected by a nut 17' to a supply tube 18 which is provided with a plurality of supply ports 19 in the bottom portion thereof. Each supply tube 18 is positioned within a diffusion baffle 20 and projects through a bore 21 in a side of the diffusion baffle 20 to connect with the nipple 17. A plurality of diffusion baffles 20 are supported on the bottom plate 13 of tank 10, but spaced therefrom, by the spacer washer 24 which has a zig-zag configuration as is best seen in FIG. 4. The supply tube 18 positioned within the diffusion baffle 20 has the supply ports 19 thereof aligned with an elongated opening 19' in the bottom wall 21 of the diffusion baffle 20. As will be seen in FIG. 4, the supply ports 19 are separated from each other by the spacer washer 24 so that the flow pattern from each supply port 19 is independent of the flow from other ports so long as the flow remains below the diffusion baffle 20. It will be seen that the sidewalls 22 of adjacent diffusion baffles 20 provide a flow path for the fluids introduced into the tank through supply ports 19 which has a restricted cross-sectional area adjacent the bottom of the tank and smoothly increases in area as the distance from the bottom plate 13 increases. The turbulence and agitation of the fluidized bed material thus gradually decreases as the flow rises into the tank 10.

In some cases, the inflowing waste liquid will contain substantial amounts of dissolved gases and there is a tendency for such gases to effervesce and collect in the upper portion of the supply tubes 18. To rid the system of these gases a vent tube 26 is provided connected to the top of the supply tubes 18 and communicating with the interior thereof through the port 28 provided in the upper side of the supply tube 18.

It will be appreciated that while the reactor has been shown with a fluid distributor characterized in that each diffusion baffle 20 has a supply tube cooperating with it, it is also possible to employ a structural arrangement of the fluid distributor such that a supply tube is provided for only every other diffusion baffle 20, so that the intermediate baffles are, so to speak, dummies. However, the faces 22 of such dummy diffusion baffles would nevertheless cooperate with adjacent diffusion baffles 20 to provide the desired gradual diffusion of flow into the fluid bed reactor.

FIGS. 5 through 7 show a modified form of the fluid distributor in which the tank bottom 33 is in the nature of a false bottom with the true tank bottom 35 spaced from the false bottom 33 by a series of structural support members 37. The false bottom 33, the true tank bottom 35 and the sides of the structural members 37 form conduits 39 for introducing waste liquid beneath the false tank bottom 33. The false tank bottom 33 is provided with a plurality of ports 41 which provide communication between the conduits 39 and the interior of the tank 10. The diffusion baffles 20 in this case are each supported on an I-shpaed member 45 which not only supports the baffle 20 but divides the flow from the double row of ports beneath each baffle, so that the flow from one row of ports goes to one side of the baffle while the flow from the other row of ports passes to the other side of the baffle.

A further modification of the flow distributor of this invention is shown in FIG. 8 in which the incoming flow is provided below the false bottom 33 of the tank 10. Nozzles 51 are provided in the false bottom 33 projecting into the waste fluid conduit 53. Spacer washers 24 are provided for supporting the diffusion baffles 20 in spaced relation from the false bottom 33 and for separating the flow which enters the tank 10 through the nozzles 51. As will be noted the projection of the nozzles 51 into the conduits 53 provides a volume at the top of the conduits 53 where dissolved gas which comes out of the fluid may collect. A vent tube 57 is connected to this top portion of conduit 53 through port 58 for disposing of or recycling this gas.

FIGS. 9 and 10 show a modified version of the fluid distributor of this invention for use in a cylindrical tank. In this case the diffusion baffles 120 are concentric arcuate members. The arcuate diffusion baffles 120 are supported on arcuate zig-zag spacer washers 124 which perform the same function as the spacer washers 24, earlier described, in supporting the diffusion baffles in spaced relation from the false bottom 133 of the tank 100 and for separating the flows from the ports 119. The central member of the fluid distributor is a frusto-conical member 150 which is supported by a cruciform member 151. The flow beneath the frusto-conical member 150 through ports 119 is as indicated by the arrows in FIG. 9, radially outward from beneath the frusto-conical member.

FIGS. 11 and 12 show a further arrangement for use in cylindrical tanks in which the diffusion baffles 160 are arranged in radial fashion and connected to a central fluid inlet chamber 166. In this case waste fluid is introduced into a tank 100 through the inlet pipe 162 which is connected to a port 165 located in the center of bottom plate 133 of the tank. The port 165 connects to an inlet chamber 166 which is in turn connected to conduits 167 each of which is connected to an interior supply pipe in one of the diffusion baffles 160 in a manner similar to that described in connection with the embodiment of FIG. 1. A spacer washer 144 is provided for supporting the baffle 160 in spaced relation from the bottom member 133 and for separating the flows from the ports 169 as has been previously described. A vent pipe 154 is connected to the supply tube in a manner similar to that shown in FIG. 3 for the purpose of disposing of any dissolved gas which comes out of solution in the supply tube.

In the showing of the radial baffles at "A" in FIG. 11, the baffles are narrow near the center of the tank and become wider as distance from the center of the tank increases in order to maintain the general configuration of the flow path between adjacent baffles. This results in a broad, inactive, surface area at the top of the baffles on which sand and debris may accumulate. At "B" in FIG. 11 is a further modification of the baffle to avoid this disadvantage, wherein the top thereof is uniformly narrow but the angle of the sloping sides decreases with increasing distance outwardly on the tank radius.

In FIGS. 13 to 16 a further embodiment of the invention is disclosed in which the diffusion baffles are integral with, or actually form, the bottom of the reaction tank, while the rest of the flow distributor structure is readily removable from the tank. Thus the tank bottom 181 is crenellated in form so that the diffusion baffles are provided as an integral part thereof. The tank bottom may be a suitably shaped plate of metal such as carbon steel, for example, or it may be concrete poured against a mold to conform to the desired shape. As seen in FIGS. 13 and 14, the flow diffuser 182 is formed by the walls 184 and 186 of adjacent diffusion baffles with a connecting strip 183 of tank bottom. An inlet header 191 penetrates the tank wall 200 and is suspended over the tank bottom 181. An array of feeder pipes 192 is connected to the inlet header 191 with each feeder pipe extending over a flow diffuser 182. A skirt 194 depends from each feeder pipe 192 and extends into and touches the bottom strip 183 of tank bottom 181. In FIGS. 14 and 16, the skirt 194 is seen to comprise a sandwich of three sheets of metal or plastic, two of which are specially formed and one is a flat plate. The formed sheets 197 and 198 are positioned on opposite sides of the unformed sheet 196 and have the upset walls 202, 203 formed therein. The sheets 196 and 197, together with the upset walls 202, 203 form fluid portals 201 deverging from a nozzle 193 at the feeder pipe 192 to the widest portion thereof closely adjacent to the bottom strip 183 of the reaction tank. The unformed sheet 196 which is secured by welding or other suitable means to the formed sheets 197, 198 supports the feeder pipe by contact with the bottom strip 183 and maintains the flows from the fluid portals on one side of plate 196 separate from the flows through the fluid portals on the other side of plate 196. Vents (not shown) may be provided as required in inlet header 191 and/or in feeder pipes 192 to vent entrapped gases.

The treated liquid flows upward in the tank and is permitted to overflow a weir 31 provided in the wall of the uppermost module 12. The overflow passes into a trough which is indicated in dotted line showing by the reference numeral 33. The overflow is withdrawn from the trough 33 through the overflow conduit 34.

In operation, considering FIGS. 1-4, liquid waste is conveyed from a source (not shown) through waste fluid inlet 14, through the T-joints 16 which feed the supply tubes 18. As indicated previously, there is located in the reactor 10 a bed of sand 30 the top surface of which is indicated at 32 in FIG. 1, where the bed is in the quiescent state. The waste liquid which has reached the supply tube 18 proceeds through ports 19 in the supply tube to enter the fluid portal 15 beneath the diffusion baffle 20 formed by the bottom end wall 21 of the diffusion baffle, the reactor tank bottom 13 and the spacer washer 24. The fluid moves through the fluid portal (whose cross-section gradually increases due to the divergent walls of the spacer washer 24). Thus, the liquid, which has a relatively high velocity as it exits ports 19 slows down in its horizontal travel through the fluid portal. As the fluid reaches the space between the adjacent diffusion baffles 20 it turns upwardly as seen in FIG. 2 into the diffusion flow path 29 between the adjacent diffusion baffles 20. In this region between the baffles 20, the upward velocity of the liquid waste will gradually decrease with increasing distance from the reactor tank bottom. In FIG. 1, in the broken section of the lowest tank module 12, an effort has been made to illustrate the effect of this decreasing velocity on the particulate solids forming the fluidized bed. Thus, in the relatively high velocity region adjacent the tank bottom 13 the concentration of particles is low due to the high velocity of the liquid. Increasing density of the fluidized bed is indicated at high levels in the tank as the velocity decreases. For the sake of convenience, the two states of the particulate solids in the reactor are illustrated in this single showing, the quiescent state as indicated by the level 32 and the fluidized state as indicated by the graded concentration indicated at 30. In actual practice, the bed would be either in the quiescent state (absent liquid flow) or in the fluidized state (with liquid flow) and not in both. The characteristics of the flow in the lowest module of the reactor tank, where the flow distributor is located, are a smooth flow of uniformly decreasing velocity and of minimum turbulence. Thus, while the velocity of the fluid in the reactor is sufficiently high to maintain the particulate solids in the fluidized state, the individual particles of the fluidized solids are not subjected to an excessive number of collisions with resultant abrasion and removal of the biological growth. The liquid flow continues upwardly through the reactor tank, greatly expanding bed 30 enroute, until it reaches the topmost module 12 of the reactor tank in which a relatively clear liquid resides. This clear liquid overflows the serrated weir 31 into a trough 34' which communicates with the effluent conduit 34 for removal or recycle to the system. Means (not shown) are provided for periodically or continuously removing excess biological growth from the inert particulate solids, disposing of the biological growth, and returning the inert solids to the reactor. If the reaction is of a type in which oxygen is dissolved in the incoming liquid waste, a certain amount of this oxygen will come out of solution in the supply tube 18. Provision is made for removal of this gas through the vent hole 28, the vent tube 26 which extends from the vent hole 28 through the diffusion baffle 20 and entirely through the reactor tank, to exhaust to the atmosphere. The spacer washer 24 not only supports the diffusion baffle in spaced relation from the reactor tank bottom but also defines the side walls of the fluid portal 15. The zig-zag configuration of the spacer washer 24 provides V-shaped flow paths with the ports located at the apexes thereof. The velocity of liquid flowing through the ports 19 will therefor decrease with increasing distance from the port while the liquid is yet within the fluid portal 15.

The embodiments of FIGS. 5-12 operate in essentially the same fashion as the embodiment of FIGS. 1 through 4. FIGS. 5 through 10 show introduction of the liquid waste through a ported or false tank bottom with upward flow into the fluid portals. FIGS. 11 and 12 utilize a central inlet chamber 66 from which supply pipes 167 conduct the liquid flow radially into the diffusion baffles 160.

Where the ports are located in the reactor tank bottom it should be noted that the ports are positioned beneath the diffusion baffles at some distance from the edge of the lower end of the diffusion baffle 20. With the particulate solids or sand bed in the quiescent state, that is, when there is no waste liquid moving through the ports in the reactor tank bottom, the sand in the reactor does not reach the ports when resting on the bottom at its normal angle of repose. This prevents sifting of the particulate solids through the ports when the biological reactor is not in operation. Of course, the problem of downward sifting of the particulate solids with consequent plugging of the ports does not arise when the ports are located in a supply tube located within the diffuser baffles 20 as illustrated in FIGS. 1 and 2.

The showings of FIGS. 9 through 12 illustrate that the principles of the invention are applicable to tanks of circular cross-section as well as tanks of the rectilinear type shown in FIG. 1.

The embodiment of FIGS. 13 through 16 operate in a manner similar to the embodiments described earlier. However, in this case, it will be seen that the fluid portals 201 discharge in a vertically downward direction, the velocity of the liquid waste being gradually and uniformly slowed as the distance from the port 193 increases. Separate fluid portals are provided on opposite sides of the central dividing and supporting sheet 196. The liquid waste is discharged from the fluid portals 201 into the flow diffusers 182 formed with skirt 194 by the adjacent sloping walls 184 and 186 of the tank bottom. The liquid waste in the flow diffuser 182 is in a flow path having divergent walls and therefor is subject again to a gradual and uniform decrease in velocity as it meets and fluidizes the solid particulate matter forming the bed. In this embodiment, the ports are so located (discharging vertically downward through the fluid portal) as to minimize the possibility that the particulate solids forming the bed will sift out of the reaction tank when the operation is shut down. This advantage can be obtained by positioning the skirt so that discharge takes place at any angle in the range from vertically downward to the horizontal.

A novel arrangement and construction of a flow distributor for fluid bed reactors has been disclosed which has wide application in biological, enzymatic, ion exchange and adsorption processes and promises improved performance for reactors carryingout such processes.

Although the present invention has been described in conjunction with preferred embodiments, it is to be understood that modifications and variations may be resorted to without departing from the spirit and scope of the invention as those skilled in the art will readily understand. Such modifications and variations are considered to be within the purview and scope of the invention and appendent claims.

I claim:

1. A liquid treatment apparatus including a tank, a quantity of inert particulate solids therein, an inlet adjacent the bottom of said tank for receiving liquid for treatment, a flow distributor located proximate the bottom of said tank to direct said liquid upwardly into said tank in a manner such that the particulate solids are fluidized without excessive turbulence, said flow distributor comprising a plurality of ports opening within said tank and communicating with said inlet, fluid portals within said tank, each of said fluid portals being in flow communication with one of said ports and constituting a walled divergent flow path of increasing cross-sectional area with increasing distance from its respective communicating port whereby the velocity of liquid traversing said fluid portals from said port is uniformly diminished, said fluid portals being oriented so that the liquid flowing therein is directed at an angle in the range from the horizontal to vertically downward in said tank, flow diffusers, having flow confining walls, each in flow communication with a fluid portal at one end thereof and oriented to direct flow from said fluid portal in a generally vertically upward direction in said tank to fluidize said particulate solids.

2. The liquid treatment apparatus of claim 1 wherein the said flow-confining walls of said flow diffusers are divergent, so that the velocity of liquid flow within said flow diffusers is uniformly decreased with increasing distance from said fluid portal.

3. The liquid treatment apparatus of claim 2 wherein the angle between said flow-confining walls of said flow diffusers is from 5° to 30°.

4. The liquid treatment apparatus of claim 1 wherein said flow-confining walls of said flow diffusers are provided by a plurality of diffusion baffles positioned adjacent each other along the bottom of said tank and secured in spaced relation to said tank bottom, said diffusion baffles having a generally trapezoidal configuration in cross-section with the axis of symmetry of said trapezoidal cross-section being vertically oriented in said tank and with the vertical dimension of said crosssection exceeding twice the broadest horizontal dimension thereof, said broadest horizontal dimension of said trapezoidal cross-section being at the lower end of said baffle adjacent the tank bottom, said broad lower end of said baffle, said tank bottom and a flow directing means forming one of said portals.

5. The liquid treatment apparatus of claim 4 wherein said ports are provided in the tank bottom.

6. A liquid treatment apparatus in accordance with claim 5 wherein said ports have tubular nozzle elements therein which extend below said tank bottom so that the flow enters the nozzle element at some distance below the tank bottom thereby providing a region adjacent the underside of the tank bottom wherein gas which comes out of solution can accumulate, and means for venting said region to the atmosphere to permit escape of said accumulated gases.

7. The liquid treatment apparatus of claim 4 wherein said liquid flows into and through supply tubes provided within said diffusion baffles with said ports provided insaid supply tubes and downwardly directed through the lower end of said baffles.

8. A liquid treatment apparatus in accordance with claim 5 or claim 7 wherein said means for directing flow is a zig-zag spacer washer separating the ports from one another and supporting the diffusion baffles in spaced relation from said tank bottom.

9. A liquid treatment apparatus in accordance with claim 7 wherein said supply tube is vented at the top thereof to the atmosphere to permit the escape of entrapped gases.

10. A liquid treatment apparatus in accordance with claim 4 wherein two parallel rows of ports are provided in association with each diffusion baffle and an I-shaped member supports the diffusion baffle in spaced relation from said tank bottom and separates said ports into two distinct rows so that the flow from said ports is directed to opposite sides of said diffusion baffle.

11. A liquid treatment apparatus in accordance with claim 4 wherein said diffusion baffles are constructed and arranged in an array of concentric rings on said tank bottom.

12. A liquid treatment apparatus in accordance with claim 4 wherein said diffusion baffles are constructed and arranged on said tank bottom in an array radiating from a common center.

13. A liquid treatment apparatus in accordance with claim 1 wherein a plurality of feed pipes are connected to said inlet and extending over and spaced from the tank bottom, said feed pipes each having a depending skirt, said skirt having therein a plurality of fluid portals each communicating with a port provided in said feed pipe and having confining walls which diverge from said port to a discharge point adjacent said tank bottom.

14. A liquid treatment apparatus in accordance with claim 13 wherein said tank bottom is of a crenellated configuration presenting a series of trough-like depressions which are narrow at the bottom thereof and have divergent sidewalls so that said trough is relatively wide at the top thereof, said skirts comprising said fluid portals extending well into said troughs so that the discharge from said fluid portals is accomplished adjacent the narrow end of said troughs.

15. A flow distributor for accepting a liquid stream from an inlet and introducing said liquid stream through a plurality of ports provided in the bottom of a treatment tank containing a quantity of particulate solids to produce an upward flow of said liquid in said tank in a manner such that the particulate solids are fluidized without inducing excessive turbulence, comprising, fluid portals each communicating with at least one of said ports and constituting a walled divergent flow path of increasing cross-sectional area with increasing distance from a communicating port whereby the velocity of liquid traversing said fluid portals from said port is uniformly diminished, said fluid portals being oriented so that said flow paths direct the liquid flow therein at an angle in the range from the horizontal to vertically downward in said tank, flow diffusers, having flow-confining walls, each in fluid communication with a fluid portal at one end thereof and oriented to direct flow from said fluid portal in a generally vertically upward direction in said tank to fluidize said particulate solids, said flow-confining walls of said flow diffusers being provided by a plurality of diffusion baffles positioned adjacent each other along the bottom of said tank and secured in spaced relation to said tank bottom, said diffusion baffles having a generally trapezoidal configuration in cross-section with the axis of symmetry of said trapezoidal cross-section being vertically oriented in said tank and with the vertical dimension of said cross-section exceeding twice the broadest horizontal dimension thereof, said broadest horizontal dimension of said trapezoidal cross-section being at the lower end of said baffle adjacent the tank bottom, said broad lower end of said baffle, said tank bottom and a flow directing means forming one of said portals, said flow directing means being a zig-zag spacer washer separating the ports from one another and supporting the diffusion baffles in spaced relation from said tank bottom.

16. A flow distributor for accepting a liquid stream from an inlet and introducing said liquid stream through a plurality of ports into a treatment tank containing a quantity of particulate solids to produce an upward flow of said liquid in said tank in a manner such that the particulate solids are fluidized without inducing excessive turbulence, comprising, fluid portals each communicating with at least one of said ports and constituting a walled divergent flow path of increasing cross-sectional area with increasing distance from a communicating port whereby the velocity of liquid traversing said fluid portals from said port is uniformly diminished, said fluid portals being oriented so that said flow paths direct the liquid flow therein at an angle in the range from the horizontal to vertically downward in said tank, flow diffusers, having flow-confining walls, each in fluid communication with a fluid portal at one end thereof and oriented to direct flow from said fluid portal in a generally vertically upward direction in said tank to fluidize said particulate solids, said flow-confining walls of said flow diffusers being provided by a plurality of diffusion baffles positioned adjacent each other along the bottom of said tank and secured in spaced relation to said tank bottom, supply tubes provided within said diffusion baffles in communication with said inlet, ports being provided in said supply tubes and downwardly directed through the lower end of said baffles, said diffusion baffles having a generally trapezoidal configuration in cross-section with the axis of symmetry of said trapezoidal cross-section being vertically oriented in said tank and with the vertical dimension of said cross-section exceeding twice the broadest horizontal dimension thereof, said broadest horizontal dimension of said trapezoidal cross-section being at the lower end of said baffle adjacent the tank bottom, said broad lower end of said baffle, said tank bottom and a flow directing means forming one of said portals, said means for directing flow being a zig-zag spacer washer separating the ports from one another and supporting the diffusion baffles in spaced relation from said tank bottom.

17. A flow distributor for accepting a liquid stream from an inlet and introducing said liquid stream through a plurality of ports into a treatment tank containing a quantity of particulate solids to produce an upward flow of said liquid in said tank in a manner such that the particulate solids are fluidized without inducing excessive turbulence, comprising, a plurality of feed pipes connected to said inlet and extending over and spaced from the tank bottom, said feed pipes each having a depending skirt, said skirt having therein a plurality of fluid portals each communicating with a port provided in said feed pipe and having confining walls which diverge from said port to a discharge point adjacent said tank bottom whereby the velocity of liquid traversing said fluid portals from said port is uniformly diminished, said fluid portals being oriented so that said flow paths direct the liquid flow therein downwardly in said tank, said tank bottom having a crenellated configuration presenting a series of trough-like depressions forming flow diffusers which are narrow at the bottom thereof with divergent sidewalls so that said trough is relatively wide at the top thereof, said skirts comprising said fluid portals extending well into said troughs so that the discharge from said fluid portals is accomplished adjacent the narrow end of said troughs and the flow diffusers direct flow from said fluid portals in a generally upward direction in said tank to fluidize said particulate solids.

* * * * *